(12) United States Patent
Brady et al.

(10) Patent No.: US 7,200,612 B2
(45) Date of Patent: Apr. 3, 2007

(54) PROCESSING DATA FOR INTERPRETATION

(75) Inventors: John Michael Brady, Oxford (GB); Jacques Feldmar, Montmagny (FR)

(73) Assignee: Mirada Solutions Limited, Oxford (GB)

( * ) Notice: Subject to any disclaimer, the term of this patent is extended or adjusted under 35 U.S.C. 154(b) by 164 days.

(21) Appl. No.: 10/221,992

(22) PCT Filed: Mar. 23, 2001

(86) PCT No.: PCT/GB01/01286

§ 371 (c)(1), (2), (4) Date: Dec. 9, 2002

(87) PCT Pub. No.: WO01/71660

PCT Pub. Date: Sep. 27, 2001

(65) Prior Publication Data

US 2003/0144976 A1 Jul. 31, 2003

(30) Foreign Application Priority Data

Mar. 23, 2000 (GB) .................................. 0007156.3

(51) Int. Cl.
  *G06F 7/00* (2006.01)
  *G06F 17/30* (2006.01)
  *G06F 17/00* (2006.01)
  *G06Q 10/00* (2006.01)
  *G06Q 50/00* (2006.01)
  *A61B 5/00* (2006.01)
  *G06F 19/00* (2006.01)
  *G06K 9/00* (2006.01)

(52) U.S. Cl. .................... 707/104.1; 707/10; 705/2; 705/3; 382/128

(58) Field of Classification Search ............. 707/104.1, 707/10; 382/156, 128; 705/2, 3
See application file for complete search history.

(56) References Cited

U.S. PATENT DOCUMENTS 5,469,353 A 11/1995 Pinsky et al.

(Continued)

FOREIGN PATENT DOCUMENTS

GB 2 303 475 2/1997

(Continued)

OTHER PUBLICATIONS

Long et al, "Multimedia Biomedical Database tools for Digital X-rays", Jun. 12-14, 1998, IEEE, pp. 202-207.*

*Primary Examiner*—Don Wong
*Assistant Examiner*—Cheryl M Shechtman
(74) *Attorney, Agent, or Firm*—Karl Bozicevic; Bozicevic, Field & Francis LLP

(57) ABSTRACT

A system for improving sensor-based decision making provides for the automatic submission of data obtained locally from instrumentation (such as image data) together with the interpretation of that data, which can be the output of some software which has been checked and possibly corrected by a user according to his/her expertise, to a remote database via an internetwork. The submission to the remote database is preferably automatic so that the remote database grows over time. The local site can access the remote database to retrieve information to assist in interpretation of the locally produced data (for example similar images and their corresponding interpretations), or can retrieve updated or improved software or parameters improving the software used for processing the data. The information on the remote database can also be reprocessed by software agents to provide statistical information based on information from a variety of such local sites. The system is particularly useful in improving the interpretation of data which is difficult to interpret such as medical image data (e.g. mammographic or cardiac ultrasound data).

21 Claims, 3 Drawing Sheets

| U.S. PATENT DOCUMENTS | | | |
|---|---|---|---|
| 5,517,405 A | | 5/1996 | Haggins et al. |
| 5,709,209 A | * | 1/1998 | Friemel et al. ............. 600/447 |
| 5,769,074 A | | 6/1998 | Barnhill et al. |
| 5,908,383 A | * | 6/1999 | Brynjestad .................. 600/300 |

| FOREIGN PATENT DOCUMENTS | | |
|---|---|---|
| WO | WO 93/25971 | 12/1993 |
| WO | WO 98/10697 | 3/1998 |
| WO | WO 99/05503 | 2/1999 |

* cited by examiner

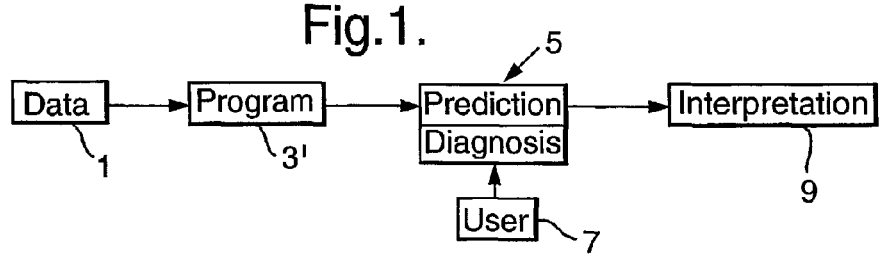
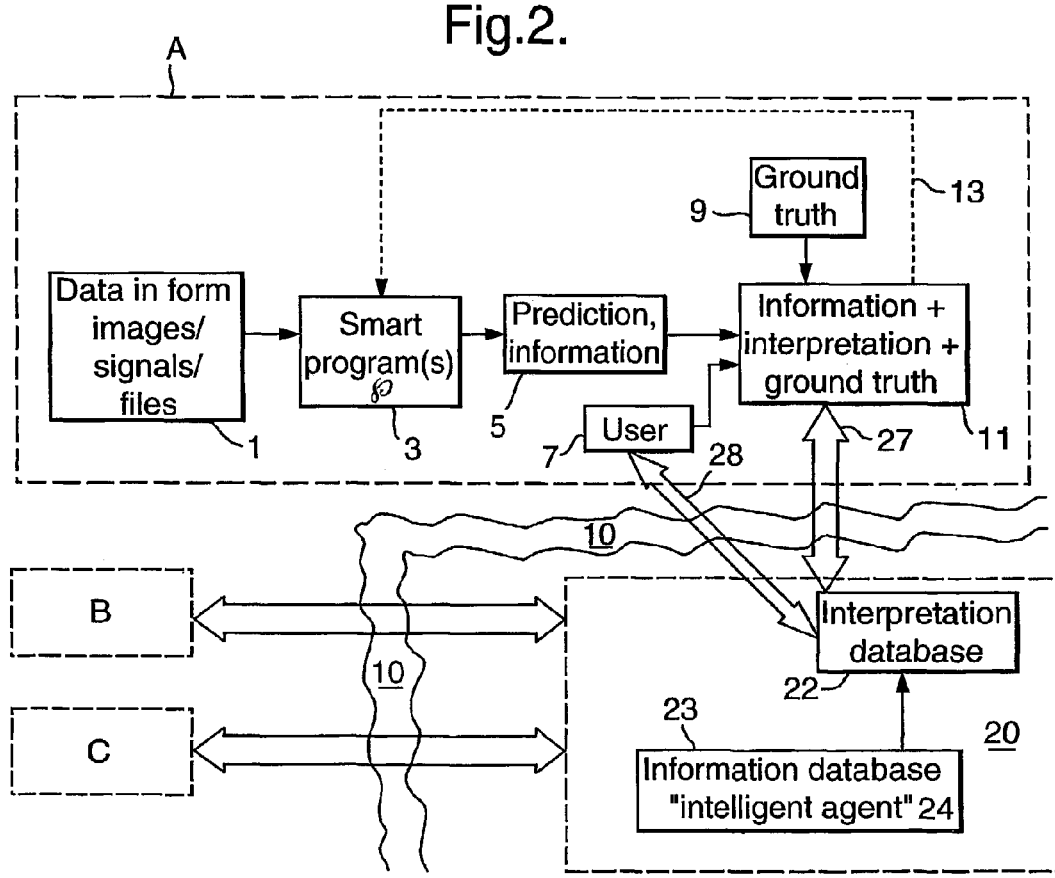

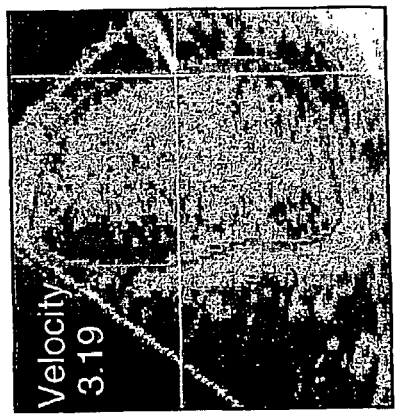
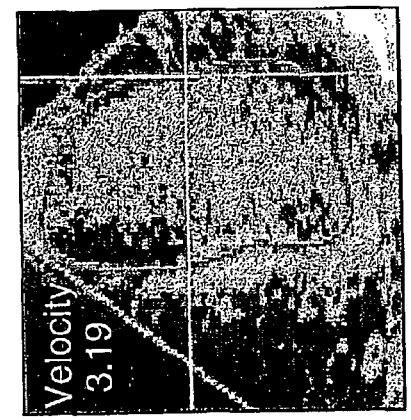
Fig.4.
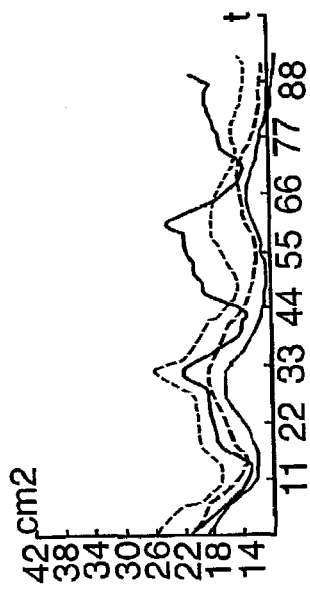
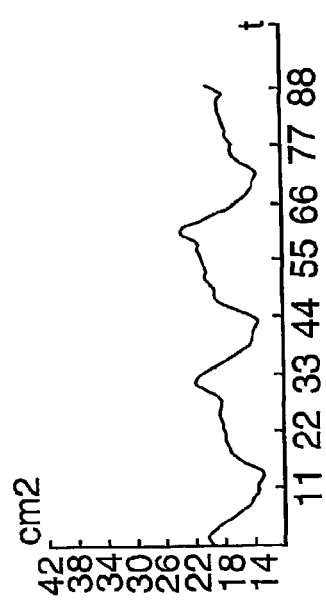
Fig.5.

PROCESSING DATA FOR INTERPRETATION

FIELD OF THE INVENTION

The present invention relates to the processing of data, in particular where a user is required to interpret the data to arrive at some conclusion.

BACKGROUND OF THE INVENTION

In many different fields, data acquired from instrumentation is required to be interpreted by a user to arrive at a conclusion. For instance, the data may be in the form of images, such as medical images, which are acquired by imaging apparatus and need to be interpreted by a clinician to allow or assist in diagnosis of the patient's condition. Other examples include sets of images of faces with the user being a law enforcement officer (who is required to identify whether a particular individual is present), and the interpretation of aerial images. Data processing software has been developed in various fields to assist in the interpretation of the data. For instance, in the medical imaging field, various types of software are available for enhancing the images or for deriving from the images information useful to the clinician.

It is important to note that the vast majority of medical image analysis systems are designed so that a physician interacts with them. There are numerous reasons for this, including the fact that physicians want at least to feel that they are in charge of the analysis, and because medical images are so complex that fully automatic solutions are rarely feasible. Consider a typical program A which utilises a set x of parameters that are to be set by the physician. We note that in general the set x varies (a) from patient to patient and (b) by physician P. We may write x(P, i) to indicate the dependence of the parameter set on the patient and on the physician=s preferences.

In almost all analyses of the results of applying any such program, but particularly if one wants to combine the results of applying the program in numerous different centres, or from a single centre but combining the results of usage by numerous physicians, for example as part of a multi-center drug trial, it is necessary to discount the idiosyncratic component of physician choice, in order to get at the underlying relationship between the image, clinical measurements made on that image and patient specific information (e.g. the patient's age, changes to the image, e.g. mammogram, since the last image was formed, the growth of a brain tumour . . . ). That is, it is necessary to factor out the effect of the particular physician. We refer to this goal as physician normalisation.

For instance, in the case of ultrasound images of the heart, software is available for processing the image data to detect the ventricular wall and to overlay on the image a contour corresponding to the wall. The software can also track the movement of the wall and provide quantitative measurements of the wall motion. User correction of the results of running such software is often necessary because the signals can be extremely poor in quality, e.g. noisy, and the image processing techniques are imperfect. For instance in the example of providing a contour overlying the image of the ventricular wall the user can correct the position of the contour by dragging it to where, on the basis of the user's experience, it should be. Different physicians will draw the initial contour slightly differently, in slightly different locations on the image. Each physician's opinion constitutes "physician truth" for him/her. In essence the image processing software generates from the image numeric values of some sort which have a geometric representation on the image (e.g. the contour). The user interacts with the geometric representation to correct the numeric values.

As a second instance, software is available for processing the image data of two image volumes (NMRI, CT, PET, SPECT, ultrasound, or a mixture of these) to place corresponding points in the two images in geometric correspondence or alignment. In this case, the physician is typically required to set a number of parameters, including a number of matching points, and/or the type of matching criterion, as well as setting thresholds, for example to segment the cranium in the case of CT images. As a third example, software is available for processing digitised images of mammograms (breast x-rays) and to determine a warping transformation that brings them into alignment. The mammograms may be of the same breast but taken at different times, or they may be of the left and right breasts of a patient. In this case, the physician may be asked to specify features in the two breast images that he/she judges to be in correspondence in order to initialise the subsequent operation of the program.

In all of these cases, the physician is required to interact with the program. In each such case the resulting analysis confounds the intrinsic anatomy or physiology that is of interest with the "physician truth" that embodies the physician's opinion. Similar considerations apply in many other fields of application than medicine. For example, images of the earth may be acquired from airplanes or satellites, and the resulting interpretation (for defense, environmental assessment, or prospecting for exploitable resources) often requires the intervention of a photointerpreter. In non-medical applications, we refer to "user truth" as a generalisation of physician truth. In what follows, physician truth should be considered equal to user truth and conversely.

Sometimes the interpretation of the data can be further assisted by the addition of "ground truth" which means information acquired from other sources and which is regarded as correct beyond reasonable doubt and thus very considerably reduces doubt and ambiguity about the data being considered. In the case of medical images, the "ground truth" may be in the form of biopsy data or information from other examinations. In the example using face images the "ground truth" may be previous sightings of the individual and, in the case of aerial images the "ground truth" may be data collected by an observer on the ground or in other ways.

This decision making process is illustrated in FIG. 1 of the accompanying drawings. It can be seen that data 1 (e.g. images or other signals or files), which can more generally be referred to as data from an "information domain", is supplied to a program 3' which produces a processed (e.g. enhanced) data set 5 perhaps by highlighting regions of an image or offering the user a tentative interpretation/diagnosis. This is used by the user 7 to produce an interpretation 9.

However, the data from the instrumentation is often extremely complex and it is difficult with such complex data to make significant improvements in the program 3 or the overall performance of the system. Furthermore, in such a system the user has an important role in framing interpretations based on the output of the program but in many cases of interest the data is complex and noisy and interpretations have to be taken on often very subtle differences. For instance, medical imaging data such as from cardiac ultrasound imaging or mammographic imaging is known to be very difficult to interpret. Although users are typically highly trained, their performance may degrade over time leading to consistent misinterpretations, or the user interaction with one type of program 3 may be worse than with a different type of program.

SUMMARY OF THE INVENTION

The present invention provides a system which improves the process of analysing data (such as images) taken at multiple centres or at a single centre but involving interactions with multiple users (e.g. physicians) by providing a method whereby user truth can be separated out from the underlying variations (e.g. anatomical or physiological) that are of primary interest. Thus the invention recognises the concept of "physician normalisation", or more generally "user normalisation", and provides a way of achieving it. It may be supposed that such a problem might be tackled using conventional methods developed, for example, in the fields of Pattern Recognition. Recall, however, that the number of parameters that determine the outcome of, e.g., a medical image analysis program is typically large so that it would in general be infeasible to conduct sufficiently many "training" examples involving a single user (physician). The method proposed herein overcomes this difficulty by allowing the program, user, or both to benefit from a wide pool of information relating to the particular information domain under consideration. This can be achieved by using a network, which may be an internetwork such as the Internet, to access a database which may be remote, and which stores information from multiple users. The database may be accessed on the basis of the data set produced by the instrumentation, the processed data, or user input (or any combination of them), to retrieve data and/or software which can mediate (i.e. improve) the processing of the data by the program or the interpretation of the data by the user.

Thus in more detail the present invention provides a method of processing data comprising: accepting input of data acquired from instrumentation as a data set of an information domain; and processing the data set under the control of processing software to assist in the interpretation of the data set; wherein said software comprises a software agent operative, on the basis of at least one of attributes of said data set, attributes of the processed data set and user-input, to access a database of information relating to said domain, said information being acquired via a network from a plurality of users, to retrieve data and/or software to mediate the processing and/or interpretation of said data set.

The invention may further comprise estimating automatically and quantitatively the effect of "user (physician) truth" on the data acquired using interventions with multiple expert users (physicians) in order to combine such data from multiple users whilst minimizing the confounding effects of user (physician) truth.

The database may be stored on a remote server or on a virtual server or copies may be stored on the client (user's) systems. However, the data is not acquired only from the local system, but from all of the different user systems communicating via a network.

The database may store and access the data from the users on the basis of the processed dataset, interactively validated or corrected by the user. The processed dataset may relate to quantitative values derived from the original data. For instance they may be derived by looking at changes in the data over time or between different modalities producing the data. These quantitative values can be used in the storage and access operations in the database.

For example, in the case of ultrasound images of the heart the image processing software can derive the position of the ventricular wall, and after correction or validation of that result by the user, calculate such quantitative values as wall stiffness, muscle tone, velocity etc., which are clinically significant. These quantitative values can be used in the storage of the data. Thus an inexperienced user could use wall velocity values to access the database to find other datasets with similar values and thus access the interpretation or ground truth which was associated with those earlier values. This gives guidance as to the correct interpretation of the current dataset.

Preferably the software agent not only accesses the database to retrieve data and/or software therefrom but also submits to the database the data from the current user. It is possible for it to update the database with either the original data set, the processed version of the data set (validated or interactively corrected by the user or the interpretation of the user), or any combination of them. This has the advantage that the database will grow with time. This means that the user and the processing program can benefit from a potentially massively wider pool of knowledge than is available locally to the user.

The fact that the database is updated with results from multiple users means that it grows much more quickly and can more quickly provide statistically significant results. For instance, in the field of medical imaging, in order to genuinely improve the process so that it is trusted in clinical practice it must work in more than 90%, probably 99% of cases. But typically the imaging software has many parameters and the variation in the information domain (i.e. the range of images and clinical significance of them) is very large. So a single site is unlikely to produce a statistically significant amount of data quickly enough. Also a single site may produce biased results because of a skewed population or deficient assay system or biased user. However a thousand sites, for example, pooling their pairs of <user truth/image> data in the database can produce as much data over a short period/days/months as several years from one site for typical medical imaging applications.

The mediation of the processing and/or interpretation of the data set may be achieved by either or both of updating the processing software (e.g. by replacing the software itself or by updating parameters upon which it relies for the processing), or by providing data such as interpretations from similar data sets which can guide the user. Updating of the software, e.g. by sending new processing parameters, can occur regularly as the amount of data in the database grows.

It will be appreciated that the database may comprise information produced by data processing at a plurality of geographically separate sites such as, in the case of medical imaging, different hospitals around the country or around the world, and software agents may be provided to reprocess the data stored on the database. Thus the data from different sites can be compared together, or the data produced by different sets of instrumentation or interpretations produced by different users can be compared.

Ground truth can be appended to the data set and can be transmitted to and stored in the database.

The database can be used not only to improve processing or interpretation at the local site but also to provide data that can be used to train new users of the processing programs, to allow the assessment and development of new processing programs, and to provide information to monitor the performance of and support the claimed performance of such programs.

While the examples mentioned are in the field of imaging, and in particular medical imaging, it will be appreciated that the invention can be applied to other fields where data is generated by instrumentation and is processed or enhanced to assist interpretation.

BRIEF DESCRIPTION OF THE DRAWINGS

The invention will be further described by way of non-limitative example with reference to the accompanying drawings, in which:

FIG. 1 illustrates a prior art system for processing and assisting interpretation of data;

FIG. 2 schematically illustrates an embodiment of the present invention;

FIG. 4 illustrates a further specific example of the type of output which can be provided;

FIG. 5 illustrates a further example of the type of output which can be provided.

DETAILED DESCRIPTION OF THE INVENTION

Figure 3:
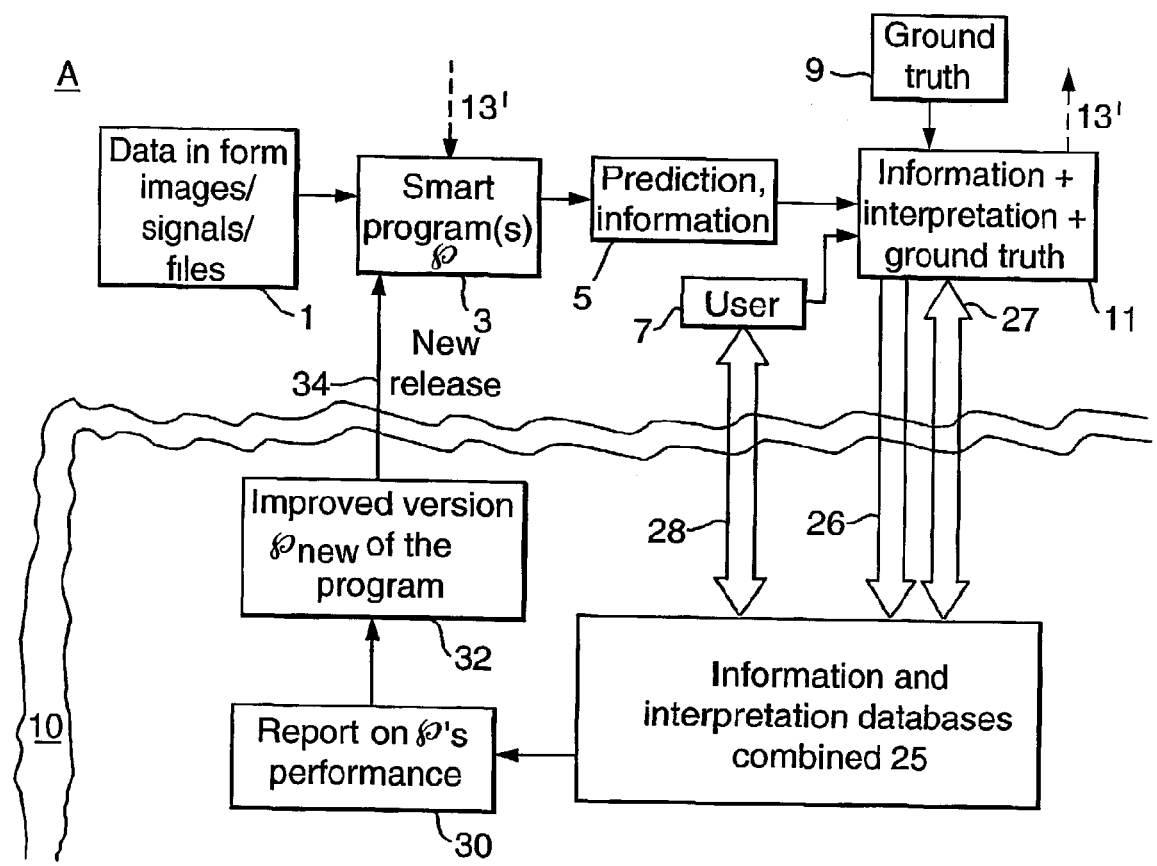
FIG. 3 illustrates a modified version of FIG. 2.

An embodiment of the invention is illustrated schematically in FIG. 2. It can be seen that the operation at the local site A is in many ways similar to that illustrated in FIG. 1, but that the local system can communicate with a database 20 and the program 3 is a "smart" program which can be improved by feedback 13. Thus the smart program 3 can learn from the "user truth" provided by local user 7 (which may itself be based partly on ground truth 9), as well as from "ser truth" derived from the database 20. Only one local user A is illustrated in detail but it will be appreciated that the system comprises a plurality of users as illustrated at B and C, at geographically separate locations. The local users A, B, C communicate with the database 20, which is illustrated as being remote from the users, via an internetwork 10 such as the Internet. The use of the Internet allows for easy accessibility. However, it is possible to arrange for communication via an intranet, a dial-up connection or other network.

The data base 20 consists of an interpretation data base 22 which stores the interpretations produced by different users and also an intelligent information data base 23 which stores a set of intelligent agents 24. The interpretation database 22 stores the processed data sets produced by the program 3 (which when corrected or validated by the user constitute "ser truth" and any ground truth, and the original data 1 from the information domain. The intelligent agents 24 stored in the intelligent information database 23 are software agents which can reprocess the data and processed data as will be explained below.

The communication between the local system and the database consists of the transfer, preferably automatically, via communication link 27 of the data set, processed data set, interpretation (user truth) and ground truth from the local system 11 to the interpretation database 22. It is also possible for the user 7 to access the database 20 by communication link 28, for instance to search for other data that resemble the locally produced data, and to download the interpretations that resulted from that other data.

The transfer via link 27 to the database at 20 can occur as part of the normal use of the local system and smart program 3. For instance, if one considers the example of the cardiac ultrasound imaging, the original data in the form of the ultrasound image is processed by the program, for instance to detect the ventricular wall. The program 3 can overlay on the image contour corresponding to the ventricular wall (examples of this are illustrated in FIG. 4). If the user is happy with the result, or after the contour has been manually edited by the user, then the user accepts it, e.g. by pressing an "OK" button and this results in the submission of the data to the database 20 via link 27. Of course actual transfer can occur later, e.g. on request from the database 20. This means that the development of the database 20 (and the performance monitoring it enables) is achieved in a way which is unobtrusive to the user. The system can also automatically seek out and submit other information e.g. the details of the cardiac ultrasound equipment (scanner) used for data acquisition, patient data, clinician etc. This would for example cover the settings of scanner, the viewing axis along which the data was acquired etc. It could also include a semi-qualitative clinician view of the quality of the image.

Of course to avoid mischievous submission of data or the submission of incorrect or unsuitable data, security or validation can be built in either at the local site A, B, C or database 20 or both. Such validation at the database could be performed by experienced users, e.g. physicians, or can be done by cross-checking between different users.

In the event of the user finding it difficult to interpret the data or to correct the contour, it is possible for the user to request (via communication link 28) other examples of similar data. The system then allows the display of the similar data alongside the locally produced data as shown in FIG. 4. Another example of such interaction is shown in FIG. 5. In FIG. 5 a graph of the velocity over time of a given part of the ventricular wall derived from the locally produced data is illustrated alongside average and standard deviation values derived from the database. The data on the database may be accessed by using the results/values of the image processing software (e.g. the wall velocities). This allows the user quickly to find earlier similar results and to access and consider the interpretations or ground truth associated with such earlier results.

As illustrated in FIG. 2 the remote database is provided with associated intelligent software agents 24 which enable additional information to be inferred from the information supplied by the local users A, B C. These agents may be implemented using neural networks or agent-based techniques familiar from Artificial Intelligence.

The intelligent agents 24 include software for providing statistical analysis of the information in the interpretation database 22, including for producing statistical generalisations about particular users, groups of users, particular processing programs or particular classes of data (e.g. particular classes of images). Furthermore, software is provided for developing training programs from the information in the database which can include user-supplied examples and examples chosen by the intelligent agent 24 from the database. Because the database 20 includes data from a large number of users, the range of examples that can be provided for such training programs is far larger and more varied than can be provided by local users alone. This is particularly important in the field of medical imaging where data from a large number of sources is needed to give statistical validity to results.

The intelligent agents 24 also allow data submitted by the users to be analysed over time so that feedback can be provided to the user or elsewhere (e.g. to regulatory authorities in the case of medical data) about their performance. The use of the database 20 in this way allows the feedback 13' to the smart program to be improved.

As with all such systems, the smart program will need to be "trained" before it becomes fully operational. This will be done by inputting "pairs" of data and associated user truth.

In the example of medical image processing this consists of image parameters and their associated physician truths. If only ground truth, from assay, is available a direct link between the diagnosis and the image data can be made. The parameters of the smart program will be regularly updated as the volume of image parameter/physician truth links increases and the statistical base becomes steadily more comprehensive and reliable. One again the ability to acquire and use the large volume of data by using the internet or similar will result in a more and more effective image analysis tool.

It will be appreciated that the system does not require a specific type of processing program 3 to be used, it is just concerned with collecting and analysing the results produced by the use of such programs. It is useful, though, to define a template so that data produced by different programs or at different sites can be properly compared. For instance, in the case of cardiac ultrasound imaging illustrated in FIG. 4 it is useful if the points on the contour produced in each data set have the same anatomical meaning and this can be achieved by, for instance, using 100 points on the contour starting from an easily recognised point such as the apex.

The use of the database allows the continuous improvement of the performance of the processing software. For instance the performance of image processing software is critically dependent upon the choice of the so-called "parameters" which it uses. The parameters are numeric values used in the image processing. For instance, in matching two images together points in the two images may be compared using a similarity function which, given a point in each image and the intensities in their neighbourhood gives a similarity score. Another common characteristic is the use of a deformation constraint. This provides a global constraint which "links together" the points being matched in the similarity function. The choice of the parameters used in such similarity functions or deformation constraints is called "parameter tuning" and this is difficult for a number of reasons:

1. The parameters are not independent ("orthogonal") so all possible values cannot be tried.

2. Parameters do not always have a real physical meaning.

3. Databases storing "ground truth", namely storing the result that the image processing should produce, or "physician truth", are quite rare.

4. The large number of parameters used by such software implies the need for very large databases giving the "ground truth".

5. The best parameters to use can be different depending on the image acquisition device, what is being imaged, and the user concerned.

By transferring the data and processed data to the database in the system described here it is possible for a large amount of ground truth and physician truth to be assembled at the database and this allows better estimation of the best parameters. Such an estimation could be run, for instance, on a regular basis and then the new parameters downloaded, or made available for download, to the local sites. Further, as well as optimising the parameters it is possible also to store the data along with information about the subject being imaged, the instrumentation being used and the user so it is possible to produce parameters which depend on this information and thus to have processing software which adapts to different subjects, different instrumentation or different users. This is all achieved without appreciably affecting the use of the processing software at the local site.

It was also noted above that the user can manually edit the processed data set (e.g. the contour). These manual changes are also transferred to the database 20 and are highly useful in tuning the parameters because they represent skilled user input from the real world. They basically transform the processed dataset into "user truth".

It is conceivable that where ground truth and user truth (e.g. physician truth) are available they are not in exact agreement. Techniques may be included for combining the user truth and ground truth into a single most likely/plausible/safest value that is "truth".

FIG. 3 illustrates a section of a modified version of the system of FIG. 2 (multiple users B and C and feedback path 13 being omitted for clarity). In the FIG. 3 system the intelligent agents 24 are supplemented by a software agent 30 which can provide a report on the performance of the smart program 3. Thus, this software agent 30 can provide a report comparing the interpretations generated by users who are assisted by a particular smart program 3 compared to the interpretations provided by those users assisted by different programs. The report can note consistent errors or shortcomings in performance and this report can be submitted both to the software company that provided the smart program and to users, authorities and purchasers, etc. FIG. 3 illustrates that the software provider can produce at 32 an improved version of the program which can be released as illustrated at 34 via the Internet 10 to the local sites A, B, C etc.

FIG. 3 also illustrates that the interpretation database and information database have been combined together into a single database 25. This could conveniently be done after an initial phase of developing and tuning the interpretation database 22 separately from the information database of intelligent agents 24 (as shown in FIG. 2).

An additional facility with systems according to the invention is the ability to use the data in the database 20 to judge what type of program 3 would give the best results for certain types of data.

The invention claimed is:

1. A method of processing data for a user, comprising:

accepting input of data acquired from instrumentation as a dataset of an information domain which dataset comprises image data which comprises medical image data; and processing the data set under the control of processing software, said processing comprising the input of "user truth" based on interpretation of the dataset by the user, to provide a processed dataset to assist in further interpretation of the dataset;

storing via a network said dataset and said processed dataset into a database of information relating to said domain acquired from a plurality of users;

estimating automatically and quantitatively the effect of said "user truth" on the data set-in order to combine in said database such data from multiple users while minimizing the effects of user truth;

and wherein said processing software comprises a software agent operative, on the basis of at least one of attributes of said dataset, attributes of the processed dataset and user-input, to access the database to retrieve data and/or software to mediate the processing and/or interpretation of said dataset by said processing software wherein the software agent is operative to transfer to the database data concerning manual adjustments made to said processed dataset by the user, and constituting said "user truth", wherein the processing of said dataset is mediated by updating said processing software using at least one of data and software from the database.

2. A method according to claim 1 wherein the storing via the network of said dataset and said processed dataset into the database is automatic.

3. A method according to claim 1 wherein the software agent comprises means for assisting the user to prepare the dataset and, processed dataset for storing in the database.

4. A method according to claim 1, wherein said database comprises information produced by execution of said method by said plurality of users at a plurality of geographically separate sites.

5. A method according to claim 4, wherein said information produced by execution of said method comprises datasets and processed datasets from said plurality of geographically separate sites.

6. A method according to claim 5, further comprising comparing together the datasets from said plurality of geographically separate sites stored on the database.

7. A method according to claim 6, further comprising storing the results of comparing together the datasets from said plurality of geographically separate sites stored on the database, and outputting the results to the plurality of geographically separate sites as said data to mediate the processing or interpretation of said dataset.

8. A method according to claim 6 wherein said datasets are processed under the control of different processing software at different ones of said geographically separate sites.

9. A method according to claim 5 further comprising processing said information in the database to generate data representing at least one of: the quality of, average values of, and principle components of said datasets or processed datasets.

10. A method according to claim 5 further comprising validating the information in said database.

11. A method according to claim 10 wherein the validation is by cross-checking between different users.

12. A method according to claim 1 further comprising accepting and associating ground truth input by the user with said datasets.

13. A method according to claim 12 wherein the database stores ground truth associated with the stored datasets or processed datasets.

14. A method according to claim 1 wherein the database stores user truth based on the interpretation of the dataset by the user.

15. A method according to claim 1 wherein said data to mediate the processing and/or interpretation of said dataset is data relating to similar datasets stored in the database.

16. A method according to claim 1 wherein said data to mediate the processing and/or interpretation of said dataset is statistical data relating to the information domain.

17. A method according to claim 1 wherein the mediation of the processing of the dataset comprises updating image analysis parameters in the processing software.

18. A method according to claim 1 wherein the information in the database is accessible by reference to the processed dataset.

19. A method according to claim 1 wherein the processed dataset comprises quantitative values derived from the dataset.

20. A computer readable storage medium carrying a computer program comprising program code means for carrying out the method of claim 1 when said program is run on a computer.

21. Data processing apparatus operative to accept input of data from a user acquired from instrumentation as a dataset of an information domain which dataset comprises image data which comprises medical image data, to process the dataset under the control of processing software said processing comprising the input of "user truth" based on interpretation of the dataset by the user, to provide a processed dataset to assist in the further interpretation of the dataset, and operative to store via a network said dataset and said processed dataset into a database of information relating to said domain acquired from a plurality of users; said software comprising a software agent operative, on the basis of at least one of: attributes of said dataset, attributes of the processed dataset and user-input, to access the database to retrieve data or software to mediate the processing or interpretation of said dataset wherein the software agent is operative to transfer to the database data concerning manual adjustments made to said processed dataset by the user, and constituting said "user truth", and wherein the system is operative to mediate the processing of said dataset by updating said processing software using at least one of data and software from the database.

* * * * *